US006310233B1

(12) United States Patent
Maurer et al.

(10) Patent No.: US 6,310,233 B1
(45) Date of Patent: *Oct. 30, 2001

(54) PRESSURE ETHOXYLATION IN DENSE GASES TO PRODUCE HYDROXYALKYL ESTER MONOMER

(75) Inventors: Charles J. Maurer, Matthews; Gordon Shaw, Charlotte, both of NC (US); Vicky S. Smith, Greenville, SC (US)

(73) Assignee: Arteva North America S.A.R.L., Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,997

(22) Filed: Nov. 4, 1998

(51) Int. Cl.[7] ........................... C07C 69/76; C07C 69/80; C07C 67/26
(52) U.S. Cl. ............................. 560/60; 560/64; 560/76; 560/96; 560/180
(58) Field of Search .................. 560/60, 64, 76, 560/96, 180

(56) References Cited

U.S. PATENT DOCUMENTS

| 3,037,049 | * | 5/1962 | Vaitekunas ........................... 230/475 |
|---|---|---|---|
| 3,052,711 | | 9/1962 | Glogau et al. ....................... 260/475 |
| 3,520,853 | | 7/1970 | Munakata et al. ................... 260/78.4 |
| 3,551,386 | | 12/1970 | Berkau ................................. 260/75 |
| 3,641,112 | * | 2/1972 | Ichikawa et al. ................. 260/475 P |
| 3,668,235 | * | 6/1972 | Ichikawa et al. ............. 260/475 PR |
| 4,271,312 | * | 6/1981 | Zimmerschied et al. .............. 560/93 |

* cited by examiner

Primary Examiner—Rosalynd Keys
(74) Attorney, Agent, or Firm—Gregory N. Clements

(57) ABSTRACT

A pressure process for preparing a hydroxyalkyl ester monomer and oligomer that can be used to prepare a polyester such as polyethylene terephthalate (PET) is disclosed. The process includes the steps of reacting, by ethoxylation, dicarboxylic acid and alkylene oxide in the presence of a compressed gas medium to form a specified mixture of monohydroxyalkyl ester and bishydroxyalkyl ester. The reaction pressure is such that the density of the gas medium is greater than or equal to half the critical density of the compressed gas medium. The mole ratio of the alkylene oxide to the dicarboxylic acid is less than about 2:1, and preferably 1.1:1.2. The DP of all reaction products is less than 5. The reactant product may be polymerized into a polyester. The process may optionally employ catalysts such as amines or amino acids. The compressed gas medium can be a solvent and an optional cosolvent. The temperature of reaction is from about 100° C. to 240° C. at a pressure of 50–5000 psi.

26 Claims, 1 Drawing Sheet

PRESSURE ETHOXYLATION IN DENSE GASES TO PRODUCE HYDROXYALKYL ESTER MONOMER

BACKGROUND OF THE INVENTION

1) Field of the Invention

The present invention relates to a process for manufacturing hydroxyalkyl ester monomers of a dicarboxylic acid which are well-known by those skilled in the art to be precursors for polyester. In general, the present invention is directed to a continuous pressure process for ethoxylating an aromatic dicarboxylic acid, e.g. terephthalic acid (TA), with an alkylene oxide, e.g., ethylene oxide (EO), without the generation of water in the reaction to form the hydroxyalky-lester monomers.

2) Prior Art

It is known in prior art synthesis of hydroxyalkyl ester monomers, such as terephthalate ester monomers (comprising bishydroxyethyl terephthalate, BHET, and/or monohydroxyethyl terephthalate, MHET) that the difficulty in formation of such esters is their limited solubility in most solvents usable in commercial practice, including water. Therefore in a heterogeneous process system in which the catalyst is in the liquid phase, a substantial rate limiting step is the migration of TA into the surrounding liquid phase so that there is sufficient contact area between the TA, EO system and the catalyst.

Another important requirement for the manufacture of these specific terephthalate ester monomers relates to the prevention of further additions of ethylene oxide or glycol to form the alkylether bonded oxygen by-products (including diethylene glycol and triethylene glycol). Eliminating the occurrence of or maintaining a low percentage yield of these by-products is required to minimize their incorporation into the polymer chain, resulting in acceptable polyethylene terephthalate (PET) resin properties such as chemical stability, color stability, thermal stability, crystallization and dyeability properties.

There have been two approaches to the production of BHET for PET from EO and TA based on whether one begins with highly purified TA, or with lower purity TA. If lower purity TA is used, a purification step for the BHET product is required. By-products produced remain with the monomer unless this purification step is undertaken. Little attention has been given to developing a viable commercial route from lower purity TA.

Ethoxylation of high purity TA without isolation or purification of the esterification product is disclosed in U.S. Pat. No. 3,520,853 to Munakata et al. Therein, an amine catalyzed, non-aqueous ethoxylation of TA is disclosed which is conducted in an organic solvent at from 80° C. to 130° C. The Munakata et al. process is conducted at a mole ratio of EO:TA of 2:1 and higher, such that conversion of TA is predominantly to BHET. Removal of EO is conducted at atmospheric pressure at a temperature no higher than 180° C. until the residual EO is below about 0.06 mole per mole of the BHET or less according to a specified equation. The preferred amount of solvent used is 20% to 200% by weight based on the weight of the TA, and it is taught that there is reduced formation of by-product at this solvent level so long as the residual EO is brought below the specified level before the temperature is raised above 180° C. for the polycondensation step.

A process for producing a monomer having a specified carboxyl:hydroxyl end group ratio is described in U.S. Pat. No. 3,551,386 to Berkau. Berkau found that when reacting dicarboxylic acids with glycols (an esterification reaction) under any suitable reaction conditions, the critical objective is to obtain a prepolymer having a CEG:HEG ratio of from 0.05 to 0.46. A monomer having this ratio range undergoes polymerization at a faster rate, however with a CEG:HEG ratio of above 0.46, the polymerization rate drops to near zero because under the conventional conditions of vacuum polycondensation, there are insufficient hydroxyl end groups to increase the degree of polymerization (DP). A faster reacting monomer would be of industrial importance.

An aqueous ethoxylation process to produce BHBT is disclosed in U.S. Pat. No. 3,052,711 to Glogau et al., using a pipe reactor, wherein a salt of TA is reacted continuously with EO with a short exposure to high temperature and the product is cooled immediately thereafter to avoid a high incidence of by-product formation. From about 1.8 to 2.8 moles of EO per mole of TA is fed continuously to the reaction zone with from about 6 to 20 moles of water and a water soluble base material. The predominant esterification product obtained is BHET with a small amount of MHET, at about a 10:1 mole ratio of BHET:MHET.

On the basis of the repeating unit for polyethylene terephthalate:

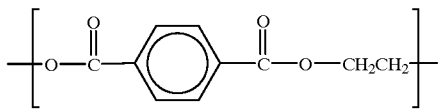

the mole ratio of EG (ethylene glycol) and TA is one (1). The mole ratio of the starting materials EG and TA in BHET which has the following structure:

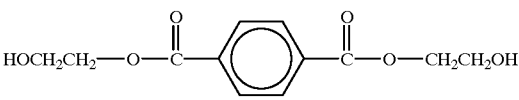

is two (2) whereas the mole ratio of the starting materials in MHET, which has the following structure:

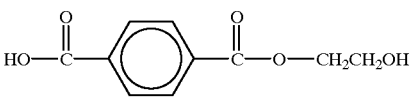

is one (1). The BHET and MHET ester monomers can be obtained by reacting either EG or EO with TA. Water is evolved when EG is used while no water is generated when EO is employed. In the present invention, 'overall mole ratio' refers to the mole ratio of glycol or glycol precursors (for example: EO) to dicarboxylic acid. Specifically, in a mixture of TA, MHET and BHET, an overall mole ratio of EG to TA is calculable from the mole percent of each component contained in the mixture. Thus, a mixture consisting of TA, MHET and BHET which has an overall mole ratio of EG to TA of 1.2 and which contains 30 mole % unreacted TA, cannot contain more than 50 mole % BHET. Note that for the calculation of mole ratio, both reacted and unreacted TA are included. To clarify, we illustrate the calculation for this mixture below.

| Component | Moles in Product (basis 100 moles total) | Equivalent Moles EG | Equivalent Moles TA |
|---|---|---|---|
| MHET | 20 | 20 | 20 |
| BHET | 50 | 100 | 50 |
| TA | 30 | 0 | 30 |
| Total |  | 120 | 100 |
| EG:TA mole ratio |  |  | 1.2 |

SUMMARY

In accordance with a basic provision of the invention there is provided an alkylene oxide based pressure process for making a hydroxyalkyl ester. The pressure in the process satisfies the following equation:

$$0.1 \leq P/Pc \leq 10$$

where P is the absolute pressure in the reaction zone and Pc is the critical pressure of the gaseous medium. Below 0.1 the gas medium is not "dense" enough to provide adequate solubility characteristics for the process required, and does not allow optimum reaction process conditions to be achieved, and above 10 requires very expensive equipment such that the overall process economics are commercially unattractive. Also the reaction zone is operated at conditions such that the density of the compressed gas medium is greater than or equal to one half of the critical density of the compressed gas medium. If this limitation is unmet, the gas medium would not be of sufficient density or solvating capacity, the desired reaction conditions could not be achieved, and there would be an insufficient amount of the gas medium to solvate the alkylene oxide or any reaction products.

It is one object of the present invention to provide a process for ethoxylation of dicarboxylic acid using alkylene oxide to form a product containing hydroxyalkyl ester monomers. These hydroxyalkyl ester monomers can react to form oligomers in a polymerization reaction having a DP greater than 1, but less than 5. A small amount of glycol and water by-products will result only from the polymerization reaction. Since the maximum DP of this invention is 5, not much by-product is produced compared to the amount of oligomers produced. Optimum conditions for the polymerization reaction differ from the ethyoxylation reaction. The monomer/oligomer product has a carboxyl end group:hydroxyl end group ratio of greater than about 0.5. If the ratio is less than 0.5 too much bishydroxyalkyl ester is formed at the expense of the preferred monohydroxyalkyl ester.

In particular, the process comprises reacting less than 2 moles, preferably no more than about 1.2 moles, of alkylene oxide per mole of dicarboxylic acid in a compressed gas medium in a zone operating at a specified temperature and pressure to form a mixture (collectively, a 'monomer'). If TA and EO are used the monomer comprises at least 20 mole % MHET, less than 50 mole % BHET and hydroxyalkyl ester oligomers, and up to about 30 mole % of unreacted dicarboxylic acid (i.e. TA). The overall preferred mole ratio (as defined previously) of diol components (derived from the alkylene oxide):dicarboxylic acid in the product is maintained in a range of from 1.0 to 1.2, and the DP average of the ester monomers and any oligomers is less than or equal to five (without further reaction). The process is conducted under conditions such that the mole ratio of MHET to BHET is greater than about 0.3.

In one specific embodiment, a tubular ethoxylation zone is provided to produce low mole ratio monomer (alkylene oxide:dicarboxylic acid mole ratio of from 1:1 to 1.2:1) in which pure or impure dicarboxylic acid is contacted with alkylene oxide in an amount of less than 2 moles alkylene oxide per mole dicarboxylic acid to form a monomer product which contains a major proportion of MHET and a minor proportion of BHET, including the steps of removing dicarboxylic acid impurities from the ethoxylation zone effluent, and separating impurities from the gaseous effluent.

In the broadest sense, the present invention comprises a process for reacting dicarboxylic acid with alkylene oxide by ethoxylation, in a compressed gas medium, at a pressure such that the density of the gas medium is greater than or equal to half the critical density of the compressed gas, at a mole ratio of less than about 2 moles of the alkylene oxide per mole of the dicarboxylic acid, at suitable reaction conditions to produce hydroxyalkyl ester monomers without the generation of water, the monomers having a carboxyl end group: hydroxyl end group ratio of greater than about 0.5; and continuing the process reaction to produce hydroxyalkyl oligomers derived from the monomers, wherein the monomers and oligomers have a number average DP of less than 5.

DESCRIPTION OF THE PREFERRED EMBODIMENTS

Figure 1:
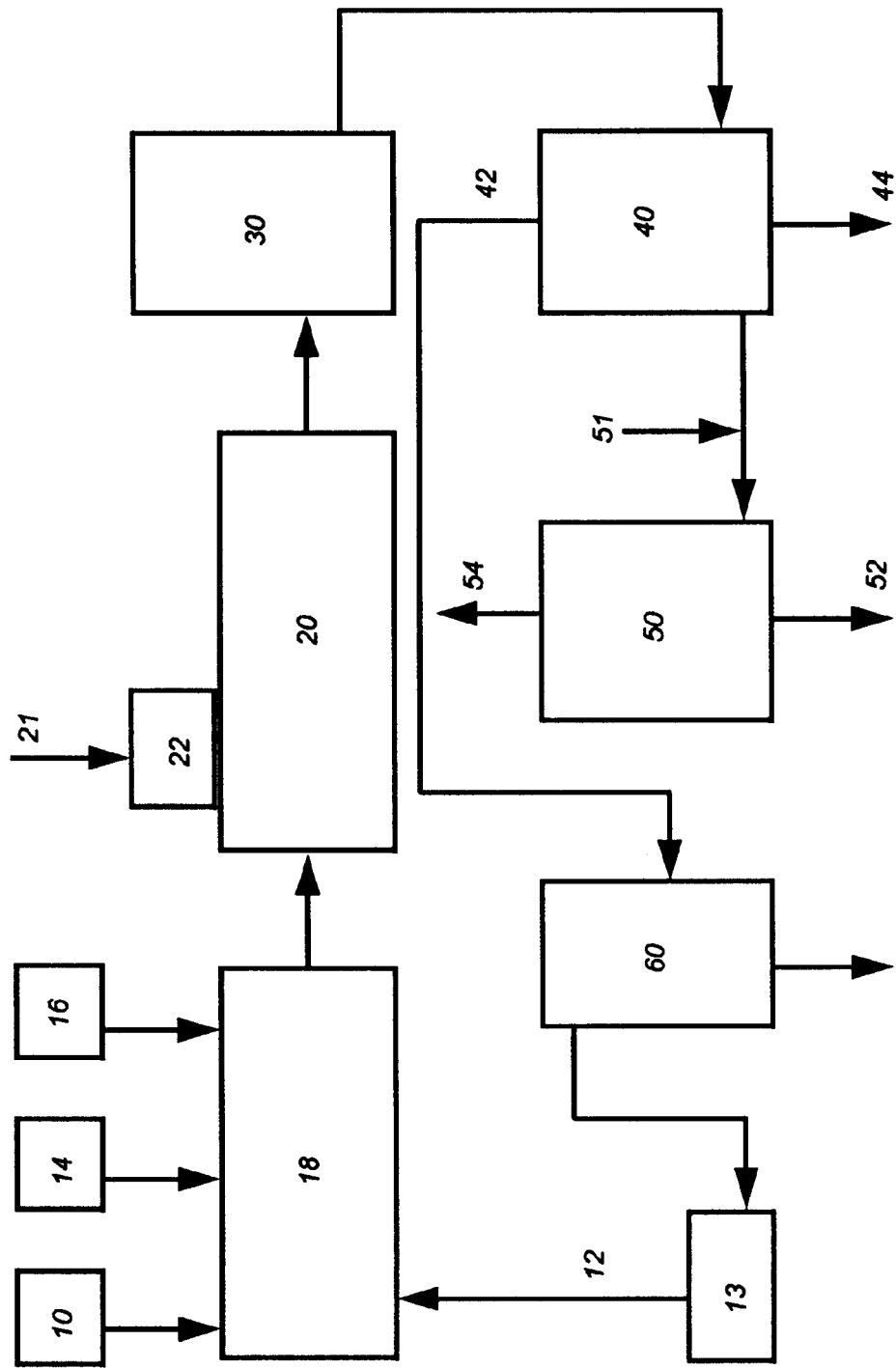
FIG. 1 is a flow diagram described hereinbelow of an embodiment of the present invention for the production of terephthalate ester monomer and/or oligomer from reacting with alkylene oxide using compressed gas.

The present invention provides a process of reacting one or more dicarboxylic acids with one or more alkylene oxides in the presence of a compressed gas solvent to produce a hydroxyalkyl ester monomer and perhaps hydroxyalkyl ester oligomers, in the presence of an optional catalyst and/or an optional cosolvent. The process is particularly advantageous for producing a highly reactive monomer for making polyester. It is preferred to make the monohydroxyalkyl ester at the expense of bishydroxalkyl ester. The mole ratio of monohydroxyalkyl ester to bishydroxyalkyl ester is at least 0.3 or higher. The higher the mole ratio of the monohydroxyalkyl ester to the bishydroxyalkyl ester, the fewer side reactions that occur during subsequent polymerization when the reaction products of this ethoxylation reaction are used as the starting material for the polymerization.

Typical alkylene oxides (AO) are ethylene oxide, propylene oxide, butylene oxide, or mixtures of two or more of these. Examples of dicarboxylic acids include terephthalic, isophthalic, phthalic, sebacic, malonic, azelaic, glutaric, suberic, succinic, adipic, bibenzoic, oxalic, pimelic, maleic, fumaric, those derived from naphthalene, anthracene, anthraquinone and biphenyl, and hemimellitic acid, or mixtures of these. The dicarboxylic acid component also includes anhydrides derived from any of the previously mentioned dicarboxylic acids, or mixtures of anhydrides, or mixtures of dicarboxylic acid anhydrides and dicarboxylic acids. In the production of PET, ethylene oxide (EO) is the alkylene oxide and terephthalic acid (TA) is the dicarboxylic acid. The amount of AO reacted is from 1.0 to less than 2.0 moles per mole of dicarboxylic acid reacted (1:1 to 2:1), preferably from 1:1 to 1.5:1, and most preferably 1:1 to 1.2:1.

The compressed gas medium of this invention is preferably a carbonaceous compound other than an alcohol or dicarboxylic acid. This gas medium is preferably an oxygenated and/or an organic compound which has an atmospheric boiling temperature of less than 1 80° C., more preferably less than 100° C., and most preferably less than 0° C. The gas medium may also be based on nitrogen or sulfur or a mixture of any of the compounds set forth herein. Examples include dimethyl ether (DME), carbon dioxide ($CO_2$), acetone, methylethyl ether, diethyl ether, methylethyl ketone, propane, sulfolane, ethylene carbonate, propylene carbonate, butane, iso-butane, ethane, pentane, iso-pentane, nitrogen, and mixtures of these. In one embodiment the medium is made up of a gaseous oxygenated organic solvent and a cosolvent. The cosolvent may be water and/or any of the previously mentioned gaseous mediums, formamide, methanol, tetrahydrofuran, dimethyl ether, dimethylformamide, acetonitrile, propionitrile, acetone, and methylethylketone. In a particular embodiment, a medium containing more than 50 mole % carbon dioxide and less than 50 mole % of an oxygenated organic solvent is used to react less than 2 moles of EO per mole of TA.

Suitable catalysts include primary, secondary, and tertiary amines and quaternary ammonium salts, as well as amino acids, or mixtures of these. Amine catalyst can be diethylene triamine, triethyl amine, trimethyl amine tripropyl amine or mixtures of these, for example. An amino acid catalyst can be lysine. The amount of catalyst used in the reaction (if any catalyst is used at all) ranges from about 0.001 to about 0.10 moles per mole of AO, preferably from 0.005 to 0.05 moles per mole AO.

The ethoxylation reaction is conducted at a temperature range of 100° C. to 240° C. and the pressure is in a range of 50–5000 psia.

In the preferred embodiment of the invention, EO and TA (in a molar ratio of less than 2:1) are reacted in the presence of a compressed gas solvent medium to produce a hydroxyethyl ester product. In the most preferred embodiment, the invention includes reacting EO and TA at a molar ratio of from about 1:1 to about 1.2:1, in the presence of a compressed gas medium at a suitable temperature and pressure, and in the presence of an amount of catalyst sufficient to produce a hydroxyalkyl ester monomer and optionally with some hydroxyalkyl ester oligomer with an overall product mixture of low DP.

The desired reaction products (including unreacted dicarboxlyic acid) of the present invention (mono- and bishydroxyalkyl ester monomers and optionally, but less preferred, a minor amount of oligomers—less than about 5 mole % based on total reaction product(s)) are designed to be polymerized to form polyester or copolyester with as few as possible by-products. To achieve this, the reaction products including unreacted dicarboxylic acid must have a CEG (carboxyl end group):HEG (hydroxyl end group) ratio of greater than 0.5. If the ratio is less than 0.5, too much bishydroxyalkyl ester (and perhaps some corresponding oligomers) is formed at the expense of the desired mono-hydroxyalkyl ester (and perhaps some corresponding oligomers). The reaction products of the present invention have a monohydroxyalkyl ester monomer to bishydroxyalkyl ester monomer molar ratio of at least 0.3 or higher. In a perfect theoretical sense, the most desired reaction product is 100% monohydroxyalkyl ester monomer. The least desired reaction product within the process of the present invention, is 100 mole % bishydroxyalkyl ester monomer and corresponding bishydroxyalkyl ester oligomers. Between these two boundaries are various combinations of mono- and bis-hydroxyalkyl ester monomer, with and without some corresponding oligomers, and with and without some portion of unreacted starting materials, such as dicarboxylic acid.

FIG. 1 is a diagram illustrating a process of the present invention for reacting dicarboxylic acid and alkylene oxide. In general, alkylene oxide (10), a compressed gas solvent medium (12), an optional cosolvent (14), and an optional catalyst (16) are combined in a dilution chamber (18) to form a feed mixture. Dicarboxylic acid (21) is added through a rotary pressure lock hopper (22) to the feed mixture in the mixing vessel (20) where mixing devices form a slurry. In the continuous process, predetermined feed rates of alkylene oxide, compressed gas medium and optional catalyst are combined and mixed, such as with in-line mixers, to form a feed stream containing (for the case of $CO_2$) in the range of 1–20 pounds, more specifically 2–10 pounds and preferentially 3–8 pounds of gaseous medium per pound of alkylene oxide along with a predetermined feed rate of optional catalyst. The stable slurry made in the mixing vessel (20) is then fed into a tubular ethoxylation reactor (30) at a rate depending on the reactor volume and reactor temperature. The monomeric reaction products are transferred to a separation vessel (40) where the pressure is reduced and the compressed gas medium, any cosolvent(s), catalyst(s), and volatile by-products are diverted as a gaseous overhead stream (42). The gaseous stream (42) is transferred to a gas clean-up unit (60) where the compressed gas solvent and any unreacted alkylene oxide are separated from the catalysts, cosolvents, volatile by-products, and decomposition products, and are recycled through a compressor (13). Monomer and perhaps minor amounts of low DP oligomer (44) can also be removed at this stage from the separation vessel (40) or converted to higher molecular weight oligomers (52) in reactor (50) where the water of reaction is removed (54) if the temperature of reactor (50) is at a temperature greater than the temperature in the tubular ethoxylation reactor (30), and any separated glycol vapor can be returned to the vessel to permit overall mole ratio control.

In one embodiment the dilution chamber (18) is a pressure vessel. The pressure and temperature of the feed mixture in the dilution chamber are selected to provide a dense fluid mixture of alkylene oxide and compressed gas medium at a temperature low enough for a stable feed mixture and at a pressure such that the density of the compressed gas medium is at or above its critical density (Dc), where the critical density is the density of a fluid at its critical temperature and critical pressure.

When the alkylene oxide is EO, the EO concentration in the compressed gas medium in dilution chamber (18) is critical and must be less than 60 mole % of the total gas phase to limit the formation of diethylene glycol in the product. For example, on a mass basis, in the case of a $CO_2$ medium, the maximum amount of EO processed is 1.5 lbs. per lb. of $CO_2$. Preferably less than 41 mole % EO in the gas phase is employed. The compressed gas solvent medium may include up to 40 wt. % of a cosolvent, which may be one or more of the following: formamide, methanol, tetrahydrofuran, dimethyl ether, dimethylformamide, acetonitrile, propionitrile, acetone, methylethyl ketone and water. The temperature and pressure in the dilution chamber vary depending on the gas medium and cosolvent employed.

A suitable ethoxylation catalyst for reacting the ethylene oxide and terephthalic acid is fed to the dilution chamber (18). The fluid components are mixed together in the dilution chamber (18) for a time sufficient to achieve a homogeneous fluid; generally 5 minutes is sufficient to prepare the diluted fluid reaction mixture.

The diluted fluid reaction mixture is fed into the mixing vessel (20), which is a pressure vessel such as a roto-feed mixer. Dicarboxylic acid (21) is added to the fluid reaction mixture to form the monomer reaction mixture, which, in the case of TA, is a slurry. Solid TA, for example, is fed into the mixing vessel (20) through a rotary pressure lock hopper (22). The mixing vessel (20) may comprise one or more mixers to form a stable reaction mixture slurry. The operating temperature and pressure in the mixing vessel (20) can be the same as or different than those in the dilution chamber (18). Preferably the pressure in the mixing vessel (20) is about the same as the reaction pressure in the tubular ethoxylation reactor (30) and the temperature in the mixing vessel (20) is less than the reaction temperature in the tubular ethoxylation reactor (30). The temperature in the mixing vessel (20) must be low enough to provide a stable slurry to feed to the tubular ethoxylation reactor (30). Generally, the preferred temperature is such that the density of the gaseous medium in the mixing vessel (20) is equal to or greater than its critical density, Dc.

The stable slurry made in the mixing vessel (20) is then fed into a tubular ethoxylation reactor (30) at a rate depending on the reactor volume and reactor temperature. The elongated tubular ethoxylation reactor (30) is operated in a temperature range of from 110° C. to 180° C. at a constant throughput or in preselected temperature zones along its length. After the slurry heats up to reaction temperatures a preferred constant temperature between 150° C. to 170° C. is employed. The residence time of any portion of the reaction mixture flowing through the reactor is less than about 30 minutes, preferably from 5 minutes to 20 minutes. The preferred pressure in the tubular ethoxylation reactor should be high enough so that the density of the compressed gas medium is equal to or greater than one-half of its critical density—Dc, and more preferably between the pressures required to compress the gas to a density of from 0.8 Dc to 1.9 Dc. Given that gas density tends to decrease as temperature increases, the higher the reaction temperature, the higher the pressure required to achieve a density greater than 0.5 Dc. Note that the actual value of the critical density is unique to the particular gas medium employed.

Table I shows the preferred conditions in the mixing vessel (20) and in the tubular ethoxylation reactor (30) when $CO_2$ is the compressed gas medium. To determine optimal operating parameters (temperature, pressure) for the mixing vessel (20) and tubular ethoxylation reactor (30), the temperature of reaction is chosen. For the selected reaction temperature, the minimum reaction pressure required to achieve a density of 0.5 Dc of the compressed gas medium is found. In the preferred experimental embodiment, the pressure in the mixing vessel (20) is the same as the pressure in the tubular ethoxylation reactor (30). Once the pressure in the mixing vessel (20) is determined, the maximum mixing temperature to achieve a desnsity equal to the Dc of the compressed gas medium is determined. Thus for the reactions described herein, the maximum mixing temperature and minimum reaction pressure are a function of the Dc of the gaseous medium.

TABLE I

Preferred Mixing and Reaction Conditions with Carbon Dioxide

| Mixing (vessel 20) Density = Dc ($CO_2$) = 0.472 gm/mL | | Reaction (vessel 30) Density = 0.5Dc ($CO_2$) = 0.236 gm/mL | |
|---|---|---|---|
| Mixing Pressure, psia | Maximum Mixing Temperature, ° C. | Selected Reaction Temperature, ° C. | Minimum Reaction Pressure, psia |
| 1800 | 59 | 110 | 1800 |
| 2000 | 67 | 130 | 2000 |

TABLE I-continued

Preferred Mixing and Reaction Conditions with Carbon Dioxide

| Mixing (vessel 20) Density = Dc ($CO_2$) = 0.472 gm/mL | | Reaction (vessel 30) Density = 0.5Dc ($CO_2$) = 0.236 gm/mL | |
|---|---|---|---|
| Mixing Pressure, psia | Maximum Mixing Temperature, ° C. | Selected Reaction Temperature, ° C. | Minimum Reaction Pressure, psia |
| 2200 | 74 | 150 | 2200 |
| 2400 | 81 | 170 | 2400 |

Depending on the initial conditions, and when employing TA, EO, $CO_2$, catalyst(s), and cosolvent(s), the resultant products from the tubular ethoxylation reactor (3) include MHET, less than 50 mole % BHET and other hydroxyethyl terephthalate oligomers, up to 30 mole % unreacted TA, and less than 3% by weight of oligomeric diethylene glycol and free diethylene glycol. A small amount of free ethylene glycol (from BHET reacting with itself, for example) as well as water (from MHET reacting further, for example) may also be present such that the total product comprises 100 mole %. Preferably all the EO is reacted. However, any unreacted EO can be recycled, and the MHET/BHET ratio can be adjusted by changing the amount of EO reacted, the reaction temperature or other reaction conditions, or the preferred reaction product based on EO and TA, comprises MHET, not more than 40 mole % BHET, and not more than 30 mole % unreacted TA. The liquid monomeric products (44) from the separation vessel (40) including with any unreacted TA and oligomeric by-products are transferred to a polyesterification reaction vessel (not shown). Alternatively, the monomereic products together with any oligomers and any unreacted TA can be esterfied in a reactor (54), as is conventional known, to a low DP oligomer before transferring to a polymerization vessel (not shown). If needed, ethylene glycol (51) is combined with the product stream from the separation vessel (40) to make up the feed stream to reactor (50), raised to a temperature suitable for polyesterification wherein water is evolved and removed (50) by conventional means.

Other compressed gases can be used to affect the invention. For example, dimethyl ether (DME) has been investigated. The critical properties of dimethyl ether are: critical density, Dc=0.274 gm/mL, critical temperature, Tc=127° C., and critical pressure, Pc=779 psia. Because the critical density of DME is lower than the critical density of $CO_2$, the preferred minimum reaction pressures are lower with DME than with $CO_2$.

Table II shows the preferred conditions in the mixing vessel (20) and in the tubular ethoxylation reactor (30) when DME is the compressed gas medium. For given mixing pressures, the maximum temperatures required to achieve a density equal to the Dc of DME are shown. Also, for selected reaction temperatures, the minimum reaction pressures required to achieve a density of 0.5 Dc are shown.

TABLE II

Preferred Mixing and Reaction Conditions with Dimethyl Ether

| Mixing (vessel 20) Density = Dc (DME) = 0.274 gm/mL | | Reaction (vessel 30) Density = 0.5Dc (DME) = | |
|---|---|---|---|
| Mixing | | 0.137 gm/mL | |
| Pressure, psia | Maximum Mixing Temperature, °C. | Selected Reaction Temperature, °C. | Minimum Reaction Pressure, psia |
| 550 | 93 | 110 | 550 |
| 730 | 114 | 130 | 730 |
| 860 | 130 | 150 | 860 |
| 980 | 140 | 170 | 980 |

Even though the DME critical density is achieved in the mixing vessel (20), it is more preferred to limit the mixing zone temperatures to less than or equal to 90° C. for embodiments where catalyst is mixed with the reactants in the dilution chamber (18). Limiting the mixing zone temperature in this way prevents the ethoxylation reaction from occurring prematurely in the mixing vessel (20).

EXPERIMENTAL

The exemplary embodiments below were performed in semi-batch and batch reactors. The invention is not so limited, however, and may be operated in continuous mode. Other possible reaction processes include plug flow, continuous stirred tank, multiple stirred tank equivalents, complete back mixed tanks, and external recirculation.

The reactions described below in Examples 1–3 were conducted in a 25 milliliter (mL) cylindrical semi-batch reactor, fabricated from Type 304 stainless steel. The reactor was equipped with entrance and exit ports for the pressurized gas and reagents, a pressure gauge, a thermocouple, and an external heater. High pressure syringe pumps were used to supply the reactor with reagents. Fluids leaving the reactor passed through a pressure control valve, which served to regulate the pressure in the reactor, and then through a thin, helically coiled stainless steel tube with a diameter of 1/16 inch which was suspended in an oil bath heated to approximately 150° C. This tube controlled the rate of pressure reduction of the exiting fluid stream, to limit chilling of the valve due to expansion of the compressed gas. The tip of the tube was immersed in a vial containing about 30 mL of methanol, for collection and analysis of the monomer product. The valve and its associated plumbing were also heated externally with heating tape to prevent chilling of the valve.

Alternatively, the pressure control valve was omitted and the effluent from the reactor was combined with a stream of methanol at room temperature supplied by a pump. The pressure in the reactor was then controlled by setting the flowrate of the methanol. This mixture was then passed through the coil of 1/16 inch diameter tubing at 150° C. into a collection vial as described above.

The general procedure for conducting a reaction was as follows. A reactor was loaded with TA and catalyst as described in Examples 1–3 below. The reactor was sealed and heated to the reaction temperature at ambient pressure. When the reactor had reached the desired temperature, the reactor was pressurized to the desired operating pressure with the designated compressed gas solvent, and then flow of the solvent gas, EO, and cosolvent began. The reactor contents were not stirred during the reaction. The pressure control valve was adjusted as necessary to maintain the desired operating pressure. The collection vial containing methanol was changed every five minutes for sample analysis in order to monitor the rate and selectivity of the reaction as a function of time. The products in Examples 1 and 2 were analyzed primarily by high pressure liquid chromatography (HPLC), with a $C_{18}$ column (5 micron) and UV/vis (ultraviolet/visible frequency range) detection. The particular conditions used in the HPLC unit comprised a column of length 250 mm, a diameter of 4.6 mm, operating at room temperature, and with a liquid flow rate of 1 mL/minute. Samples from the collection vial were diluted to 1% concentration with a mixture containing 80% diluted acetic acid and 20% acetonitrile for injection into the HPLC. (The acetic acid used in the sample preparation contains 99% water and 1% acetic acid). The products in Example 3 were analyzed by proton Nuclear Magnetic Resonance (NMR) analysis at 300 MHz, where samples were diluted in pyridine-d5, for analysis of DEG, unreacted TA, oligomers, and ethylene glycol.

All of the following Examples contain measured amounts of starting materials (reactants, solvents, cosolvents, catalyst) to yield a CEG/HEG ratio, including unreacted TA, of greater than about 0.5, and a monohydroxyalkyl ester monomer to bishydroxyalkyl ester monomer molar ratio of greater than about 0.3, provided that the reaction conditions were suitable and the reaction was substantially completed. Examples 3 and 4 did not meet the claimed limitations for the reasons set forth later.

EXAMPLE 1

The reactor described above was loaded about one-third full with glass wool, to ensure uniform flow and prevent channeling throughout the cross section of the reactor. Five grams (gm) of TA were then poured on top of the glass wool plug. Fifty microliters ($\mu$L) of diethylenetriamine (the catalyst) was added on top of the TA. More glass wool was then added to fill the remaining reactor volume and prevent the TA and catalyst from being disrupted by solvent flow during the course of the reaction.

The reaction was then conducted using the procedure described above with the temperature maintained at 150° C. and the pressure maintained at 5000 pounds per square inch (psi). The pressure control valve was used to control the pressure in the reactor. Carbon dioxide ($CO_2$) with a single component density of 0.548 gm/mL at reaction conditions was used as the solvent gas and flowed continuously through the reactor at a rate of 4 mL per minute where the flow rate was measured at the syringe pump used to supply the $CO_2$. The barrel of the syringe pump was cooled to approximately 0° C. and the pressure in the pump was 5000 psi, hence the flow rate cited in this example is that of liquid, compressed $CO_2$ exiting the pump. 0.5 mL per minute of EO and 1.0 mL per minute of formamide cosolvent were also pumped through the reactor. The flow rates of the latter two compounds are those of a liquid at room temperature exiting the pump. Because of the elevated temperature of the reactor, the volumetric flow rates of $CO_2$, formamide, and EO are greater in the heated zone than at the pump heads, but the mass flow rates are the same.

Flow continued for 42.5 minutes. During the course of the run 16.78 millimoles of product, consisting of a mixture of MHET and BHET, were produced corresponding to 55.8% conversion of TA to product. The molar ratio of MHET to BHET in the product was 0.364. HPLC measurements did not show a significant diethylene glycol (DEG) peak.

EXAMPLE 2

A glass wool plug and 5 gm of TA were added to the reactor as described in Example 1.50 μL of diethylenetriamine was dissolved in 1 mL of diethyl ether and applied evenly over the top of the TA bed. A glass wool plug was added to the top, and the reactor was sealed and preheated to 150° C. as described in Example 1. The reaction was then conducted using the procedures described in Example 1 with the temperature maintained at 150° C. and the pressure at 5000 psi. Dimethyl ether (DME) with a single component density of 0.556 gm/mL at reaction conditions was used as the solvent gas, and formamide was used as a cosolvent. The flow rate of DME, measured at the pump at approximately 0° C., was 5 mL per minute and the flow rates of formamide and EO, measured at the pump at room temperature, were each 0.5 mL per minute.

Flow continued for 45 minutes. A total of 2.63 millimoles of product consisting of MHET and BHET was produced corresponding to 8.8% conversion of TA to product. The molar ratio of MHET to BHET in the product was 3.15. HPLC measurements did not exhibit a significant DEG peak.

EXAMPLE 3

The reactor was loaded with 5 gm of TA and 50 μL of diethylenetriamine dissolved in 1 mL of diethyl ether, sealed and heated to 150° C. as described in Example 2. The pressure in the reactor was controlled by setting the flow rate of a stream of methanol which was combined with the effluent stream from the reactor. The reaction was then conducted using the procedures described in Example 1 with the temperature maintained at 150° C. and the pressure at 5000 psi. $CO_2$ was used as the solvent gas with a flow rate of 5 mL per minute measured at the pump at approximately 0° C. Acetonitrile was used as the cosolvent; the flow rate of acetonitrile was 1 mL per minute and the flow rate of EO was 0.5 mL per minute, both measured at the pump at room temperature. Flow was maintained for one hour, after which the EO flow was stopped while the $CO_2$ and acetonitrile flows were maintained for another 15 minutes in order to remove all products from the reactor. The combined effluent was evaporated to dryness, washed with diethyl ether and air-dried overnight. 1.14 gm of product were recovered, corresponding to 14.2% conversion of TA to product. The molar ratio of MHET to BHET in the product was 0.08. While this molar ratio is below and outside the claimed range of the present invention, the Example does demonstrate that acetonitrile has solvating properties with respect to the reaction materials.

An NMR spectrum showed that the product contained, in addition to MHET and BHET, 2.1 weight % DEG (including its esters with TA), small quantities of unreacted TA, and low molecular weight oligomers of polyethylene terephthalate and ethylene glycol.

EXAMPLES 4–9

The next set of experiments illustrates the low DEG values achievable by the invention. All experiments in Table III were performed in the one liter reactor except Example 9, which was conducted in a 50 mL reactor. In each of these experiments, TA, triethylamine catalyst (TEA), and water cosolvent were added to the reactor. Air was flushed out of the reactor, the reactor was sealed, and DME was added until the set-point pressure was reached. The reactor was then heated to the reaction temperature and EO was added. Addition of the EO initially caused the vessel pressure to increase, then as the EO reacted the pressure returned to the original set-point pressure. The reaction proceeded for the designated time, after which the reactor was cooled and vented to ambient pressure. The reaction products were dissolved in methanol and analyzed by HPLC, NMR, and gas chromatography (GC). Table III gives the results and reaction conditions.

TABLE III

Experimental Results with Water Cosolvent and DME Fluid

| No | TA gm | TEA gm | $H_2O$ gm | EO gm | DME gm | Temp ° C. | Press psi | RT min | M/B mole ratio | TA conv (%) | DEG NMR Wt % | DEG GC wt % |
|---|---|---|---|---|---|---|---|---|---|---|---|---|
| 4 | 166 | 2.0 | 8.0 | 26.1 | 396 | 150 | 1200 | 104 | 0.16 | 23.3 | 1.80 | — |
| 5 | 166 | 2.0 | 8.0 | 26.1 | 396 | 130 | 1200 | 104 | 0.49 | 11.7 | 1.00 | — |
| 6 | 83 | 1.0 | 4.0 | 21.8 | 370 | 150 | 1400 | 30 | 1.11 | 5.6 | <1.00 | 0.27 |
| 7 | 83 | 1.0 | 8.0 | 21.8 | 370 | 150 | 1400 | 30 | 0.97 | 8.0 | <1.00 | 0.24 |
| 8 | 83 | 1.0 | 24.0 | 21.8 | 370 | 150 | 1300 | 30 | 0.76 | 13.4 | <1.00 | 0.28 |
| 9 | 8.3 | 0.11 | 2.6 | 1.8 | 30 | 170 | 2500 | 10 | 0.65 | 33.4 | <1.00 | 0.69 |

Included in Table III are the reaction times (RT), molar ratio of MHET to BHET (M/B) produced, the amount of DEG measured by NMR and GC, the reaction temperature, the amount of TEA used, the amount of water cosolvent, and the amount of DME fluid solvent. Although Example 4 has a M/B ratio below and outside the claimed range, it shows larger reactor times and perhaps higher temperatures tend to favor the formation of BHET and higher levels of DEG in these Examples.

EXAMPLES 10–16

The reaction was simulated in continuous mode with a computer model. The model simulates the monomer-forming reaction in a tubular reactor of specified internal diameter and temperature, given specified inlet concentrations (TA, catalyst) and solvent flowrates (EO, DME or $CO_2$, water). The model uses reaction rate constants determined from experimental data to calculate the amount of MHET and BHET generated during the reaction given the specified inlet conditions. Inlet conditions and results are shown in Table IV below. Water was used as a cosolvent for Examples 11, 13, and 14, and TEA was used as a catalyst in Examples 10–13. Examples 14–16 were conducted with no catalyst.

TABLE IV

Continuous Flow Results from Simulation

| No | EO (g/min) | TA (g/min) | EO:TA mole ratio | DME (g/min) | TEA (g/min) | H$_2$O (g/min) |
|---|---|---|---|---|---|---|
| 10 | 5412 | 18227 | 1.12 | 89194.0 | 6.56 | — |
| 11 | 12492 | 40836 | 1.15 | 89194.0 | 15.14 | 624.6 |
| 12 | 2498 | 7854 | 1.20 | 89194.0 | 3.03 | — |
| 13 | 5830 | 18858 | 1.17 | 89194.0 | 7.07 | 291.6 |
| 14 | 40.6 | 70.4 | 1.07 | 7526.0 | — | 2.0 |
| 15 | 30.0 | 37.2 | 1.13 | 7526.0 | — | — |
| 16 | 30.0 | 37.2 | 1.29 | 7526.0 | — | — |

| No | Diam (in.) | React length (ft) | Temp °C. | Press (psia) | RT (min) | Product lb/hr | TA conv (%) | M/B mole ratio |
|---|---|---|---|---|---|---|---|---|
| 10 | 5.0 | 1548 | 170 | 4320 | 30 | 1812 | 51 | 0.30 |
| 11 | 5.0 | 1637 | 170 | 4320 | 30 | 4503 | 56 | 0.30 |
| 12 | 5.0 | 1500 | 170 | 4500 | 30 | 1052 | 71 | 0.55 |
| 13 | 5.0 | 1541 | 170 | 4500 | 30 | 2514 | 70 | 0.58 |
| 14 | 2.0 | 739 | 145 | 2920 | 4500 | 12.7 | 50 | 8.90 |
| 15 | 2.0 | 640 | 170 | 4640 | 3900 | 9.8 | 51 | 6.41 |
| 16 | 2.0 | 541 | 170 | 4640 | 3300 | 9.8 | 52 | 7.20 |

Thus it is apparent that there has been provided in accordance with the invention a process for making terephalate ester monomer that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of of the appended claims.

What is claimed is:

1. A process for reacting dicarboxylic acid with alkylene oxide to produce hydroxyalkyl ester monomers and perhaps minor amounts of oligomers comprising:
    reacting dicarboxylic acid with alkylene oxide in a solvating compressed gas medium, at a pressure such that the density of the gas medium is greater than or equal to half the critical density of the compressed gas, at a mole ratio of less than about 2 moles of said alkylene oxide per mole of said dicarboxylic acid, at suitable reaction conditions to produce mono- or mono and bishydroxyalkyl ester monomers and perhaps minor amounts of oligomers, said monomers and any unreacted dicarboxylic acid having a carboxyl end group: hydroxyl end group ratio of greater than about 0.5; and wherein the mole ratio of monohydroxyalkyl ester monomer to bishydroxyalkyl ester monomer is greater than about 0.3,
    wherein said dicarboxylic acid is selected from the class of terephthalic, isophthalic, phthalic, sebacic, malonic, azelaic, glutaric, suberic, succinic, adipic, bibenzioc, oxalic, pimelic, maleic, fumaric, those derived from naphthalene, anthracene, anthraquinone and biphenyl, hemimellitic acid, or mixtures of these; anlydrides thereof, mixtures of anhydrides, or mixtures of dicarboxylic acid and dicarboxylic acid anhydride.

2. The process of claim 1, wherein said suitable reaction conditions comprises a reaction temperature within the range of 100° C. to 240° C., and a reaction pressure within the range of 50–5000 psia.

3. The process of claim 1, wherein said suitable reaction conditions comprises a reaction pressure which satisfies the following equation:

$$0.1 \leq P/Pc \leq 10$$

where P is the absolute pressure in the reaction zone and Pc is the critical pressure said gaseous medium.

4. The process of claim 1, wherein said alkylene oxide is selected from the class of ethylene oxide, propylene oxide, butylene oxide, or mixtures of two or more of these.

5. The process of claim 4, wherein said dicarboxylic acid is terephthalic acid and said alkylene oxide is ethylene oxide.

6. The process of claim 5, wherein said hydroxyalkyl ester monomers and oligomers comprises monohydroxyethyl terephthalate, and optionally bishydroxyethyl terephthalate and hydroxyethyl terephthalate oligomers.

7. The process of claim 6, wherein said monohydroxethyl terephthalate comprises at least 20 mole % of the reaction product, said bishydroxyethyl terephthalate and hydroxyethyl terephthalate oligomers comprises less than 50 mole %, and up to about 30 mole % is unreacted terephthalic acid.

8. The process of claim 1, wherein said monomers and said oligomers (if any) have a number average DP of less than 5.

9. The process of claim 1, wherein said mole ratio of said alkylene oxide to dicarboxylic acid is in the range of 1:1 to 1.2:1.

10. The process of claim 1, wherein said compressed gas medium is a gaseous oxygenated solvent with or without a cosolvent.

11. The process of claim 1, wherein said compressed gas medium has an atmospheric boiling temperature of less than 180° C.

12. The process of claim 11, wherein said atmospheric boiling temperature is less than 0° C.

13. The process of claim 1, wherein said compressed gas medium is selected from the class of carbon dioxide ($CO_2$), propane, sulfolane, ethylene carbonate, propylene carbonate, butane, iso-butane, ethane, pentane, iso-pentane, and mixtures of these.

14. The process of claim 13, wherein said compressed gas medium comprises a solvent and a cosolvent, said cosolvent being selected from the class of formamide, methanol, tetrahydrofuran, and dimethylformamide.

15. The process of claim 13, wherein said compressed gas medium is carbon dioxide.

16. The process of claim 1, wherein a suitable catalyst is employed in the reaction.

17. The process of claim 16, wherein said catalyst is selected from the class of primary, secondary and tertiary amines, quaternary ammonium salts, amino acids, or a mixture of these.

18. The process of claim 17, wherein said catalyst is used in the reaction in a range from about 0.001 to about 0.10 moles per mole of alkylene oxide.

19. The process of claim 1, wherein said compressed gas medium is used in a range of from 1 to about 20 pounds per pound of alkylene oxide.

20. The process of claim 14, wherein said compressed gas medium is used in a range of 3–8 pounds per pound of alkylene oxide.

21. A process for reacting terephthalic acid with ethylene oxide to produce hydroxyethyl terephthalate monomers and perhaps minor amounts of oligomers comprising;
    reacting terephthalic acid using ethylene oxide in a compressed gas medium, at a pressure such that the density of the gas medium is greater than or equal to half the critical density of the compressed gas medium, wherein said ethylene oxide concentration in said compressed gas medium is less than 60 mole % of the total gas phase, wherein the mole ratio of said ethylene oxide to said terephthalic acid is less than about 1.2 to produce mono- and/or bishydroxyethyl ester monomers and perhaps minor amounts of oligomers, said monomers and any unreacted terephthalic acid having a carboxyl end group hydroxyl end group ratio of greater than about 0.5; and wherein the mole ratio of monohydroxyalkyl ester monomer to bishydroxyalkyl ester monomer is greater than about 0.3.

22. The process of claim 21, wherein said compressed gas medium is in a range of 1–20 pounds per pound of ethylene oxide and comprises a solvent and optionally a cosolvent.

23. The process claim 22, wherein said solvent is carbon dioxide.

24. The process of claim 23, wherein said cosolvent is formamide.

25. The process of claim 21, wherein said reaction includes a catalyst of triethylamine used in an amount of from about 0.001 to about 0.10 moles per mole of ethylene oxide.

26. The process of claim 21, wherein said monomers and said oligomers (if any) have a number average DP of less than 5.

* * * * *